(12) United States Patent
Haycraft

(10) Patent No.: US 8,477,308 B1
(45) Date of Patent: Jul. 2, 2013

(54) POLARIZED, SPECULAR REFLECTOMETER APPARATUS

(75) Inventor: James Joseph Haycraft, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 283 days.

(21) Appl. No.: 12/615,183

(22) Filed: Nov. 9, 2009

(51) Int. Cl.
*G01J 4/00* (2006.01)

(52) U.S. Cl.
USPC .......................................................... 356/369

(58) Field of Classification Search
USPC ............ 356/243.1–243.8, 244–246, 364–370
See application file for complete search history.

(56) References Cited

U.S. PATENT DOCUMENTS

| | | | | |
|---|---|---|---|---|
| 6,488,892 | B1 * | 12/2002 | Burton et al. | 422/82.05 |
| 2008/0186477 | A1 * | 8/2008 | Wang et al. | 356/73 |
| 2008/0212095 | A1 * | 9/2008 | van Nijnatten et al. | 356/364 |

OTHER PUBLICATIONS

James J. Haycraft, The elastic constants and related properties of the epsilon polymorph of the energetic material CL-20 determined by Brillouin scattering, The Journal of Chemical Physics, 2009, pp. 1-1 through 1-8, 131.

* cited by examiner

*Primary Examiner* — Tara S Pajoohi Gomez
(74) *Attorney, Agent, or Firm* — Charlene A. Haley; Christopher L. Blackburn

(57) ABSTRACT

An apparatus and method for use on precision refractive index experiments that are performed on individual faces of single crystals or liquid surfaces of material using specific wavelengths of light. The process is used to measure the major and minor axes of the optical indicatrix of a single crystal of material at a very specific wavelength. This process is repeated for each crystal face in order to form a complete picture of the refractive index for the sample.

17 Claims, 7 Drawing Sheets

POLARIZED, SPECULAR REFLECTOMETER APPARATUS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to precision refractive index experiments, and more specifically, precision refractive index experiments that are performed on individual faces of single crystals of material using specific wavelengths of light.

BACKGROUND OF THE INVENTION

There are a multitude of patents dealing with the measurement of refractive indices. The vast majority of those patents deal solely with measurements on liquids. The remaining patents for devices that measure refractive indices are roughly broken into two categories: reflectometers and refractometers. Reflectometers use light reflection to make measurements and refractometers rely on the refraction of light to make measurements.

The following patents describe refractometer devices capable of measuring the refractive index of solid samples. U.S. Pat. Nos. 2,383,347, 4,692,024, 5,572,314, and 7,199,871. The following patents describe reflectometer devices capable of measuring the refractive index of solid samples, U.S. Pat. Nos. 3,402,631, 3,751,162, and 4,899,055. The following patents do not really fall into the exclusive categories of refractometer or reflectometer, yet are still devices capable of measuring the refractive index of solid samples, 2004/0233434 A1, U.S. Pat. Nos. 7,292,389, 6,037,579, 6,937,333, and 6,924,893.

U.S. Pat. No. 6,181,427 "Compact Optical Reflectometer System" describes a device for collecting reflectance data and images from a sample. The optical path includes a spectrometer for measurement of properties other than refractive index. It is to be used with thin films, not crystalline samples. U.S. Patent Ser. No. 2003/0086083 A1, "Optical Metrology tool with dual camera path for simultaneous high and low magnification imaging" describes a device for imaging the surface of a sample at two levels of magnification. This particular device lacks the ability to make reflectance measurements, which can be used to calculate refractive indices.

U.S. Pat. Nos. 7,099,081, 7,248,362, and Patent Application US2006/0197948AI "Small-Spot spectrometry instrument with reduced polarization and multiple-element depolarizer therefore" describes a device which contains illumination and collection optics. This instrument is primarily designed to look at thin films or wafers of material, not crystalline samples.

The following patents describe light scattering devices operating at scattering angles of 90 degrees and/or 180 degrees: U.S. Pat. Nos. 6,643,012, 6,025,918, US 2004/0145735, U.S. Pat. Nos. 5,661,557, 4,575,629, 5,373,358, 5,684,580, 5,088,820, 4,586,819, 4,505,586, 6,850,323, 3,469,920, 4,080,073, 5,870,188, 6,307,625, 5,999,255, 6,205,354, 5,949,532, 7,039,452, 6,868,285, 6,281,971, 5,607,643, 5,869,346, 5,753,449, 6,667,070, 5,621,523, 6,545,755, 4,648,714, Re. 34,153, U.S. Pat. Nos. 4,008,961, 6,795,177, 6,747,735, 5,991,653, 5,841,139, 5,351,250, 4,269,509, 4,197,009, 4,270,864, 6,897,951, 4,620,284, 3,704,955, 5,751,289, 4,068,953, 4,127,329, 4,856,897, 5,247,343, 5,786,893, 2,940,355, 3,807,862, 5,377,004, 6,040,906, 3,516,744, 3,542,481, 6,614,523, 3,414,354, 4,798,463, 5,442,438, 5,510,894, 4,081,215, 5,255,067, 6,352,502, US 2005/0002028, U.S. Pat. No. 5,110,204. These patents deal exclusively with light scattering phenomenon. Several of these devices employ fiber optics as part of the device, but it is usually a small contribution.

The following patents describe reflective devices where the incidence and reflective angles can be varied from approximately 0 degrees to approximately 90 degrees: U.S. Pat. Nos. 6,897,955, 4,647,207, 6,734,967, 5,608,526, 6,859,278, 4,790,659, 7,023,549, 5,166,752, 5,416,588, 6,590,656, 6,483,580, 6,753,961, 4,834,539, 5,963,327, and 4,585,348. These patents are primarily concerned with ellipsometers and other reflection-type devices, which is a much different phenomenon than light scattering. Several of the devices employ a small amount of fiber optics.

The following patents describe fiber optic devices applied to light scattering: U.S. Pat. Nos. 5,615,673, 6,486,948, 5,521,703, 6,373,567, 6,333,784, 5,911,017, 6,028,666, 6,006,001, 4,630,923, 5,765,948, 3,770,350, 6,061,134, 6,115,528, 5,751,415, 6,100,975, 5,184,521, and 5,783,389. These patents use fiber optics extensively in the light scattering process. However, these devices still gather light at scatterings angle of 90 degrees or 180 degrees.

U.S. Pat. No. 5,262,644; "Remote spectroscopy for Raman and Brillouin Scattering" describes a device for collecting Raman and Brillouin spectra remotely, using optical fibers. The sample being investigated is held in a container and the optical fibers positioned around it. The apparatus does allow the fibers to be placed at a multitude of angles, fixed into position by a ring collar. The incident fiber carries infrared light from a suitable laser source and the collection fiber takes the scattered light to various instruments and detectors. Nothing in the apparatus allows control over the polarization of the incident or scattered light. In addition, the apparatus does not appear to allow the sample container to be independently moved and aligned, relative to the fiber optic cables.

The apparatus of another device was published in the journal *Review of Scientific Instrumentation* 60(8) in August 1989 in an article entitled, "Light scattering apparatus for angular dependent studies on anisotropic materials." This device also employs a four circle apparatus with respect to the sample, but was entirely constructed of conventional mirrors and optics. The light must be steered under the rotation stage and then directed exactly perpendicular to the table surface, through the precise center of rotation of the stage. Failure to achieve this level of precision results in a beam that walks or is clipped when the rotation arm is moved from side to side, when all the incident optical components are in place. In addition, the light is directed under the arm from the center of the stage before being reflected upward and through the focusing optics toward the sample. Every mirror reflection represents a loss of light intensity, a possible change in light polarization, and an opto-mechanical mount that has to be adjusted and will eventually migrate out of alignment. The result works, but is very difficult to align and maintain. In particular, the mirror mounts tended to drift over time, meaning that the device would have to be completely re-aligned in order to be functional again. The use of so many mirrors also limited the range of motion of the rotating arm. Because the light had to be directed under the rotation stage, the mount for the sample had to be built off-center and contain multiple supports to properly distribute the weight. These supports severely limited the range of motion for the rotation arm assembly. This limitation means that the final setup did not have the capability to do a true 180 degree back scatter experiment. Finally, the placement of the pick-off beam to align the sample on an axis orthogonal to the rotation arm had the potential to send light directly down the collection optics path into the detector, causing catastrophic damage.

All of the shortcomings of the devices described above are resolved in the invention described below. An ideal light scattering apparatus and method would include a light that is steered using fiber optics, eliminating the problems associated with multiple mirrors and their mounts. The invention described below is simpler which makes it much easier to align and is also extremely stable over time, and complete re-alignments are no longer necessary. In addition, the sample is now aligned using the scattering optical axis, which means a true 180 degrees backscatter experiment is now possible, and there is very little possibility of sending intense light into the detector. The range of the rotation arm is also greatly increased, making it possible to probe all possible scattering geometries. The light polarization is always maintained and the beam does not walk and is not clipped when the rotation arm is moved. The invention described below is more flexible and adaptable than any of the prior devices.

Figure 1:
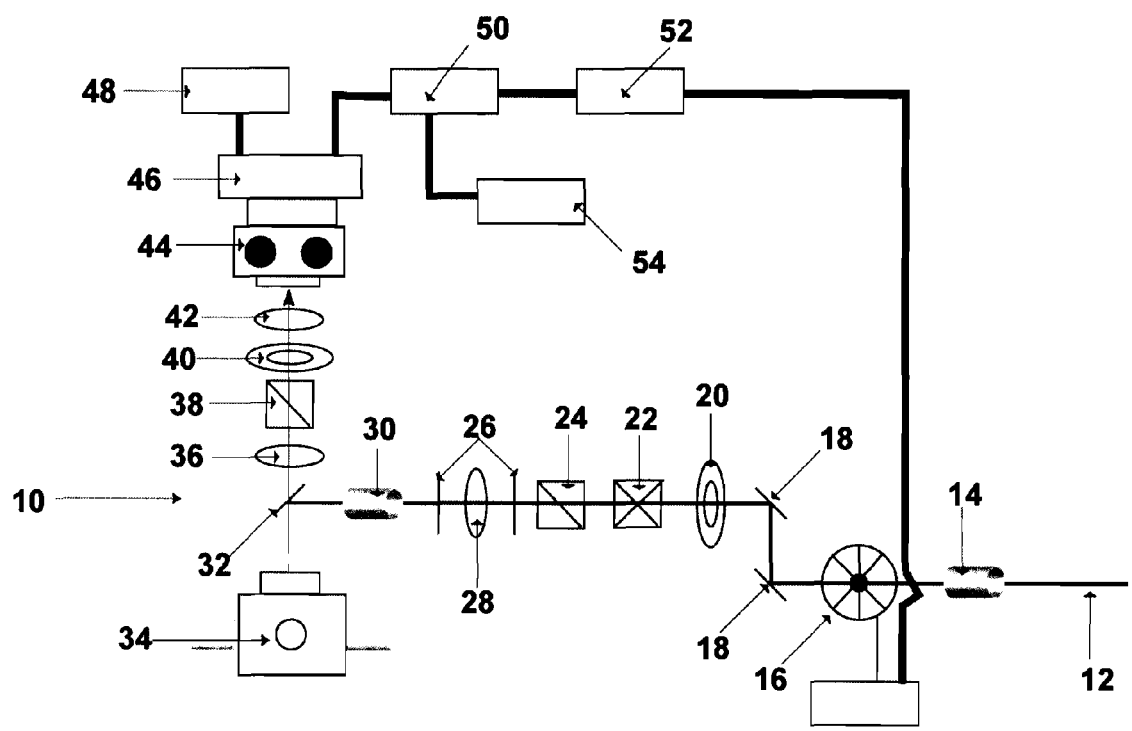
FIG. 1 is a block diagram of the instrument used to determine the principle directions in each crystal face by utilizing near-normal-incidence specular reflection, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to an apparatus and method for use of precision refractive index experiments that are performed on individual faces of single crystals of material using specific wavelengths of light. An article that is to be published after Nov. 10, 2009 titled: "*The elastic constants and related properties of the epsilon polymorph of the energetic material CL-20 determined by Brillouin scattering*" by James J. Haycraft is hereby incorporated by reference.

Embodiments of the invention generally relate to a method and apparatus including, a device that holds and/or suspends a sample in position to be analyzed, an adjustable source that produces light, an optional first light tube and an optional second light tube, wherein the light is directed through an optional first light tube, an optional optical chopper, wherein the light is directed through the chopper, wherein the exiting light from the chopper provides a signal reference for experimentation, optionally at least one mirror that directs light and aligns the light with sample and collection optics, an optional iris, an optional polarization scrambler, an optional first polarizer and/or polarization device and a second polarizer and/or polarization device, an optional first diffuser and an optional second diffuser, a first lens, a second lens and a third lens, wherein the light is directed through the first optional iris, the polarization scrambler, the first polarizer and/or polarization device, the first diffuser, the first lens, the second diffuser, and the second light tube, a glass pick-off or other beam sampling device, wherein the glass pick off reflects a small portion of the light towards the sample, wherein the light reflects of the sample and through the second lens, the second polarizer and/or polarization device, the second iris and the third lens, an optional microscope assembly, wherein the light is directed through the microscope assembly, a data collection system, a photomultiplier tube and a photomultiplier power supply, wherein after data is collected, light impacts the photomultiplier tube and the photomultiplier power supply energizes the photomultiplier tube creating a current signal, a pre-amplifier, wherein the current signal is channeled to the pre-amplifier which the current signal is converted to a voltage signal which is amplified, an optional digital locking amplifier, wherein the voltage signal is channeled to the digital locking amplifier which records the voltage signal, and an optional digital oscilloscope, wherein the modulated signal is monitored.

Another aspect of the invention generally relates to a method for measuring surface reflectivity of a sample (may be crystalline or liquid) including the steps of producing light, directing the path of light through an optional first light tube, directing the light through an optional optical chopper, modulating the light by the chopper, exiting the modulated light from the chopper providing a referencing signal, aligning the modulated light by optional mirror(s) with the sample and collection optics, directing the light through an optional first iris, an optional polarization scrambler, a first polarizer and/or polarization device, an optional first diffuser, a first lens, an optional second diffuser and through an optional second light tube, reflecting a small portion of the light toward a crystalline sample by a glass pick-off or other beam sampling device, mounting sample on a device that holds and/or suspends the sample in a position to be analyzed, rotating the device to place the sample in a desired position for analyzing, directing the light to reflect off of the sample, directing the light through a first lens, a second polarizer and/or polarization device, a second iris, and a second lens, directing the light through a microscope assembly observing the light through the microscope assembly, collecting data from findings of observing the light through the optional microscope assembly, impacting the light onto a photomultiplier tube, energizing the light/photomultiplier tube by the photomultiplier power supply which alters the light to a current signal, channeling the current signal to a pre-amplifier and converting the current signal into a voltage signal and amplifying the voltage signal, channeling the amplified voltage signal to an optional digital locking amplifier and recording the amplified voltage signal, and channeling the amplified voltage signal to a digital oscilloscope and monitoring the modulated signal.

In embodiments of the invention, where the device that holds and/or suspends a sample, it may include, but is not limited to, a multi-axis translator system. In these embodiments, the device may by rotational. In other embodiments, the data collection system is, but is not limited to, being performed by personal computer and/or direct visualization. Embodiment sample for analyzation can be crystalline structure(s) or liquid structure(s). Measurements of the invention include the apparatus measuring the surface reflectivity of a crystalline or liquid structure.

A light source is any device or apparatus capable of producing photons for use in scientific study. Examples of these devices include, but are not limited to lasers, arc lamps, and incandescent lamps. A detector is any device or apparatus capable of transforming photon energy into electrical energy. Examples of these devices include, but are not limited to photomultiplier tubes, photodiodes, and silicon detectors. A polarizer or polarization device is any device or apparatus capable of inducing or altering the polarization vector of a beam of photons. Examples of these devices include, but are not limited to, calcite polarizers, Glan-Laser polarizers, wave plates, and polarization rotators. A fiber optic is any device or apparatus capable of channeling photons along a contained straight or curved path without the use of traditional, flat surface mirrors. Examples of these devices include, but are not limited to, fiber optic cables and light tubes.

This invention is used to measure the major and minor axes of the optical indicatrix of a single crystal of material at a very specific wavelength. This process is repeated for each crystal face in order to form a complete picture of the refractive index for the sample. This is most useful for anisotropic materials of low symmetry, where the maximum value of the refractive index does not align with crystal axis.

The refractive index of a material is dependent upon both the wavelength of the light used to make the measurement and the orientation of the electric vector with respect the crystal axis. As such the bulk refractive index of a material is often quite different from the values calculated when measuring the optical indicatrix at a specific wavelength of light. For bulk refractive index measurements, it is often necessary to measure the transmittance of light through the sample, which limits the types of samples that can be measured. This device uses reflected light to make a measurement, thus allowing a larger number of samples to be probed. This apparatus is equipped with an iris, which allows the field of view to be narrowed considerably, the result of which is experimental data gathered from a specific point on the crystalline face of the sample.

Embodiments of the invention allow thin films, wafers, and crystalline samples to be measured. The addition of a rotational element to the x-y-z translation stage allows the major and minor axes to be directly measured. The use of simple optical components allows it to be easily aligned and facilitates ease of use. Any number of light sources may be employed.

Light (12) enters the apparatus through a light tube (14) before being modulated by an optical chopper (16), which provides the signal reference for the experiment. A pair of steering mirrors (18) and (18) are used to align the light with the incident optics. The light passes through an iris (20), a polarization scrambler (22), a polarizer (24), two diffusers (26), (26) and a lens (28) before passing through a second light tube (30). A small portion of the light is reflected toward the sample by the glass pick-off (32). The sample is mounted on an x-y-z translation stage with an attached rotation stage (34). The light reflects off of the sample and proceeds through a lens (36), a polarizer (38), an iris (40) and another lens (42) before entering the microscope assembly (44). The microscope assembly allows for direct viewing of the sample. When data is collected, the light leaves the assembly and impacts a photomultiplier tube (46). The photomultiplier tube is energized by the photomultiplier power supply (48). The current signal from the photomultiplier tube is sent to a pre-amplifier (50), which changes the current signal to a voltage signal and amplifies it by several orders of magnitude. This signal is then sent to the digital locking amplifier (52) for recording. A digital oscilloscope (54) is used to monitor the modulated signal from the sample.

There is an urgent need within the energetics research community to find energetic materials that give increased performance, but are insensitive to a variety of initiation methods. A number of researchers are concentrating their efforts on understanding detonation initiation by mechanical shock. Detonation can be considered to be a collective property of an energetic material and is highly dependent on intermolecular interactions, molecular arrangements, and molecular composition. The strength of the interactions between the molecules comprising a molecular crystal has a measurable effect on the macroscopic properties of the solid. These properties can often be correlated with the strength of the lattice interactions through the elastic constants. An example is the energetic material pentaerithrytol tetranitrate (PETN) whose stiffest elastic constant is $C_{11}$, and whose lowest detonation sensitivity is along the a-crystallographic axis. For this area of research, it is the lattice interactions that are of primary interest because they hold the answer to how mechanical energy is transferred not only from one part of the solid to another, but also from the lattice to the molecules. This transfer of energy is necessary for the initiation of decomposition reaction that then leads to the subsequent detonation.

To gain understanding of the mechanism of detonation initiation by shock initiation, a series of studies on mechanical properties has been undertaken on several energetic materials. Recently, comprehensive studies on the elastic properties at ambient conditions of the energetic materials cyclotetramethylene tetranitramine (HMX) and cyclotrimethylene trinitramine (RDX) were reported. 2,4,6,8,10,12-hexanitro-2,4,6,8,10,12-hexaazatetracyclo[$5.5.0.0^{5,9}.0^{3,11}$] dodecane ($\epsilon$-CL-20), is a similar secondary explosive and therefore is a logical choice for comparison of elastic properties to those of other energetic materials, with the aim of understanding how those properties relate to detonation initiation. There has been one previous report on the elastic constants of $\epsilon$-CL-20. Xu et al. published a study using molecular dynamic simulations to study surface interactions of pure $\epsilon$-CL-20 and $\epsilon$-CL-20 based PBXs. Included in their publication is a calculated set of stiffness constants for a simulated single crystal of $\epsilon$-CL-20.

The elastic properties of the energetic material CL-20 were determined by Brillouin scattering. In the next section, a brief introduction to Brillouin scattering is given. All 13 elastic constants of CL-20 are presented and compared to the published theoretical work. This is followed by a discussion of several specific elastic constants and linear compressibilities. Finally, a comparison to the stiffness constants of HMX and RDX is presented, and the role of elasticity with emphasis on detonation sensitivity is briefly discussed.

The principles of Brillouin scattering are well documented in the literature. Brillouin spectroscopy probes acoustic phonons near the Brillouin-zone center, where the wavelengths of the phonons are of the order of hundreds of unit cells. This condition allows the material to be modeled as an elastic continuum. The inelastic light scattering utilized in Brillouin spectroscopy is the result of diffraction from sound waves caused by thermal fluctuations in the lattice. Acoustic phonons are the vibrations in the lattice associated with translations of the center of mass in the unit cell. These phonons propagate through the lattice at the speed of sound. The velocity of each phonon can be directly related to the strength of the force constants holding the molecules in the unit cell. Each acoustic phonon in the lattice has one longitudinal component and two transverse components, which means that for any given phonon propagation direction, there are a maximum of three modes that may be measured.

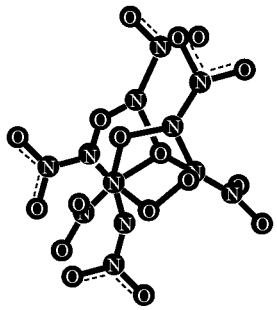

(A)

The above is a ball and stick structure of a molecule of CL-20 (A). The hydrogen atoms have been removed for clarity.

Equation (1) is the Brillouin scattering equation for an anisotropic medium. The change in frequency of the inelastically scattered light is very small in Brillouin experiments, so the frequency of the incident light is approximately equal to the frequency of the scattered light giving:

$$\delta\omega_a = \pm \frac{v_a \omega_i}{c} \sqrt{n_i^2 + n_s^2 - 2n_i n_s \cos\theta} \quad (1)$$

where $\delta\omega_a$ is the frequency shift of the inelastically scattered light, or simply the Brillouin shift, $v_a$ is the velocity of the acoustic mode in the material, c is the speed of light in a vacuum, $\theta$ is the angle between the incident and scattering wave vectors, and $n_i$ and $n_s$ are the indices of refraction of the incident and scattered light, respectively.

The Brillouin shift equation allows calculation of the acoustic velocities which can be related to the elastic constants of the lattice. Starting with the equation of motion (2), $$\rho \frac{\partial^2 u_i}{\partial t^2} = C_{ijkl} \frac{\partial^2 u_j}{\partial r_j \partial r_k}, \quad (2)$$

and then substituting plane wave solutions of the form (3)

$$u_i = u_i^0 \exp i(q \cdot r - \omega_a t). \quad (3)$$

yields the following equation (4):

$$[C_{ijkl} q_j q_k - \rho \omega_a^2 \delta_{il}] u_l^0 = 0. \quad (4)$$

where $C_{ijkl}$ are the elastic constants, $q_j$ and $q_k$ are wavevectors of the acoustic waves, $\rho$ is the density of the material, $\omega_a$ is the frequency of the acoustic wave and $\delta_{il}$ is the Kronecker delta. Operating in the long-wavelength limit, Equation (4) can be reduced to $$|C_{ijkl} q_j q_k - \rho v_a^2 \delta_{il}| = 0. \quad (5)$$

Solving this Christoffel determinant gives the eigenvalues that are then used to calculate the elastic constants of the solid.

A calculation method initially utilized for elastic constant determination of cubic crystals and oriented polymer films has been modified for use in low symmetry crystal systems. This method consists of an iterative, least squares minimization routine that solves for the elastic constants when the secular equations are experimentally over-determined from many measurements of velocities in different directions. As the program goes through each iteration, the Christoffel determinant is solved for the eigenvalues, designated $\rho v^2_{a, calc}$, for each of the experimentally determined velocities using a set of trial elastic constants. The vector of differences, e, between these eigenvalues and the corresponding quantities, $\rho v^2_{a, obs}$, from the experimentally observed velocities is then calculated. The square of the error vector (6), $$e^T e = \sum_j |\rho v^2_{a,obs} - \rho v^2_{a,calc}|^2 \quad (6)$$

is then minimized by systematically varying all of the input elastic constants until a global minimum is reached. By utilizing this calculative technique, the accumulation of experimental error is avoided while still allowing for a complete determination of the stiffness tensor.

Figure 2:
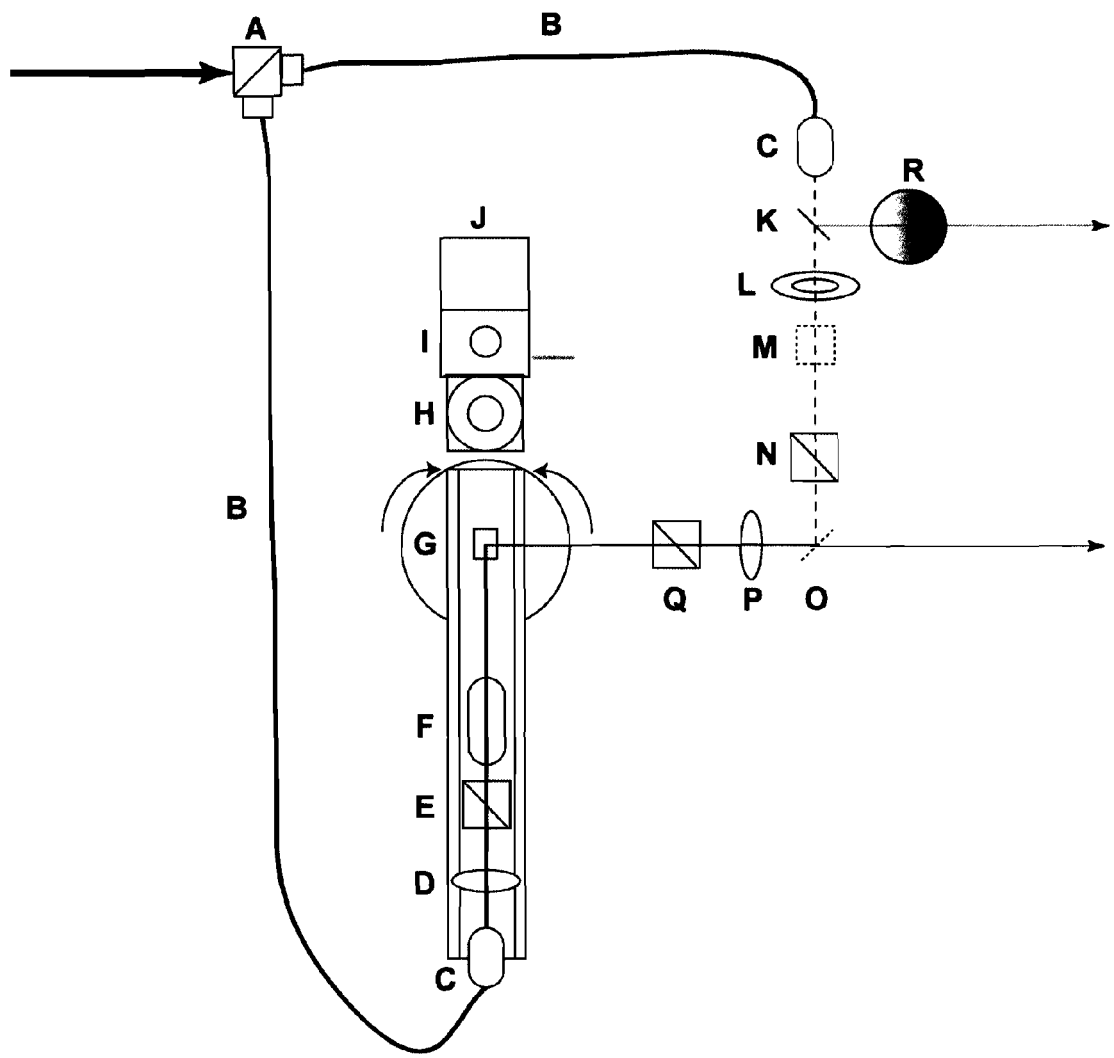
FIG. 2 is a block diagram of an embodiment of a Brillouin scattering instrument, modified to incorporate fiber optics and increase accuracy in crystal alignment, according to embodiments of the invention.

Experiment: Optical quality, untwinned, single crystals of ε-CL-20 were grown using two separate methods. The crystals grown using the first method were dissolved in methanol. The solution was filtered using a 2 micron syringe filter into a clean vial, which was placed in a small dessicator including either toluene or xylene. In method two, crystals were grown by slow evaporation at 300 K from saturated solutions of dry ethyl acetate. Both methods produced crystals of similar size, but different crystal habit. All crystals exhibited a minimum of eight well-formed faces, four of which were zonal to the c-crystallographic axis, $\{\bar{1}\bar{1}0\}$, $\{\bar{1}10\}$, $\{1\bar{1}0\}$, and $\{110\}$. Although the crystals were composed of well-formed faces, defects were noted in the interior portions of several of the crystals. Crystals of ε-CL-20 form in the monoclinic space group P2(1)/n, with lattice constants a=8.852 Å, b=12.556 Å, c=13.386 Å, and β=106.96°. There are four molecules in the unit cell. The P2(1)/n space group and lattice parameters were verified using single-crystal x-ray diffraction and were equivalent within error to those reported by A. T. Nielsen and co-workers. The Miller indices of the crystal faces are necessary to precisely define the scattering angle θ. In order to assign the Miller indices of the faces, the interfacial angles between all usable faces were determined by optical goniometry. The Miller indices were corroborated by values obtained from single-crystal x-ray diffraction FIG. 2 is a block diagram of the Brillouin scattering instrument, modified to incorporate fiber optics and increase accuracy in crystal alignment. The major components are identified as follows: 60/40 beam splitter with fiber optic couplers, fiber optic cables, collimating lens, focusing lens, Glan-Laser polarizer, polarization rotator, rotation stage with rigid optic support with a total range of motion of 215°, small rotation stage with sample support structure, three-axis positioner, rigid support, beam sampler, iris, removable beam block, polarizer, removable mirror, lens, polarizer, and neutral density filter wheel.

As shown in FIG. 2, light enters the device at the 60/40 beam splitter where it is directed simultaneously into two identical fiber optic cables. Along the first path, light exits the fiber through a collimating lens and is focused onto the sample using another lens. The degree and angle of polarization are controlled by the polarizer and polarization rotator. All of these components are mounted on a rotation stage that has a total range of motion of 215 degrees. The sample of interest is suspended beneath a small rotation stage, the position of which is controlled by a 3-axis translator system. All of these components are mounted on a rigid rod support.

For the second path, light exits the fiber through a collimating lens. A beam sampler takes a small portion of the light and directs it through a neutral density filter for use as a reference signal. The remainder of the light passes through and through an iris. A removable beam block is used to terminate the light for certain experiments. When desired, is removed and the light passes through a polarizer and then strikes a small removable mirror, where it is directed toward the sample. The light passes through a lens and another polarizer before striking the sample of interest.

In addition to a well-defined scattering geometry, the refractive indices must be determined to solve Eq. (1). Because ϵ-CL-20 is a monoclinic crystal system, the axes of the optical indicatrix are not constrained by symmetry to be coincident with all crystallographic axes. The principal directions for each unique face were determined with near normal-incidence specular reflection using a modified microspectroreflectometer, of which the basic apparatus elements are described elsewhere. An example of the apparatus is in FIG. 1. Incoming light is mechanically modulated before passing through a series of polarizers, diffusers, and lenses. The light reflecting off of the sample may be viewed directly through the microscope or sent to a photomultiplier detector to be recorded. These reflectivities were measured at 532.0 nm, the incident wavelength used in the Brillouin experiments reported here. The refractive indices for the relevant directions in the ϵ-CL-20 crystal were calculated from the single wavelength reflectivities using Fresnel's equation under the approximation that k≈0 for a clear, colorless crystal at visible wavelengths.

Brillouin scattering experiments were performed on four single crystals of ϵ-CL-20 at 296 K and ambient pressure. A four-circle, Brillouin-scattering instrument was used which allowed rotation of the incident light beam and crystal independently so that a large number of phonons can be accurately sampled. The published work was extensively modified to incorporate the use of fiber optics in the incident optical train. The apparatus details of this instrument are shown in FIG. 2. Light is directed along two separate paths in the instrument. The first path includes all of the incident optics and the rotation stage. The second path directs light to the Fabry-Pérot interferometer for a reference signal and also to the sample to aid in crystal alignment or to allow for backscatter experiments. The result of this apparatus was an instrument that held stability for weeks at a time, without degradation of the laser beam power or profile. Frequency shifts were resolved using a Fabry-Pérot interferometer operated in the triple-pass configuration. Incident laser power was set at 40-65 mW, depending on the scattering geometry. To ensure the Brillouin peaks of ϵ-CL-20 were assigned to the correct spectral order, a minimum of three free spectral ranges (FSRs) varying from 0.833 to 1.552 cm$^{-1}$ were employed on each crystal used in this study. The FSRs were calibrated using the known shift of pure liquid benzene.

Crystals were oriented in the incident light beam using back reflections from the specular input and output crystal faces. All four laboratory polarizations were utilized in each scattering geometry: Vertical-Vertical, Vertical-Horizontal, Horizontal-Vertical, and Horizontal-Horizontal, where the incident polarization setting is given first and the analyzer polarization is given last. This standard for polarization was used for clarity, but the actual polarizations were along the major and minor principal directions on each face of the crystal, which were predominantly vertical and horizontal, respectively, to the scattering plane. Each recorded spectrum was a summation of a minimum of 2000 interferometer scans.

FIG. 2. As shown in the article "Journal of Chemical Physics" the block diagram of the Brillouin scattering instrument, modified to incorporate fiber optics and increase accuracy in crystal alignment. The major components are identified as follows: (a) 60/40 beam splitter with fiber optic couplers, (b) fiber optic cables, (c) collimating lens, (d) focusing lens, (e) Glan-Laser polarizer, (f) polarization rotator, (g) rotation stage with rigid optic support with a total range of motion of 215°, (h) small rotation stage with sample support structure, (i) three-axis positioner, (j) rigid support, (k) beam sampler, (l) iris, (m) removable beam block, (n) polarizer, (o) removable mirror, (p) lens, (q) polarizer, and (r) neutral density filter wheel.

Figure 3:
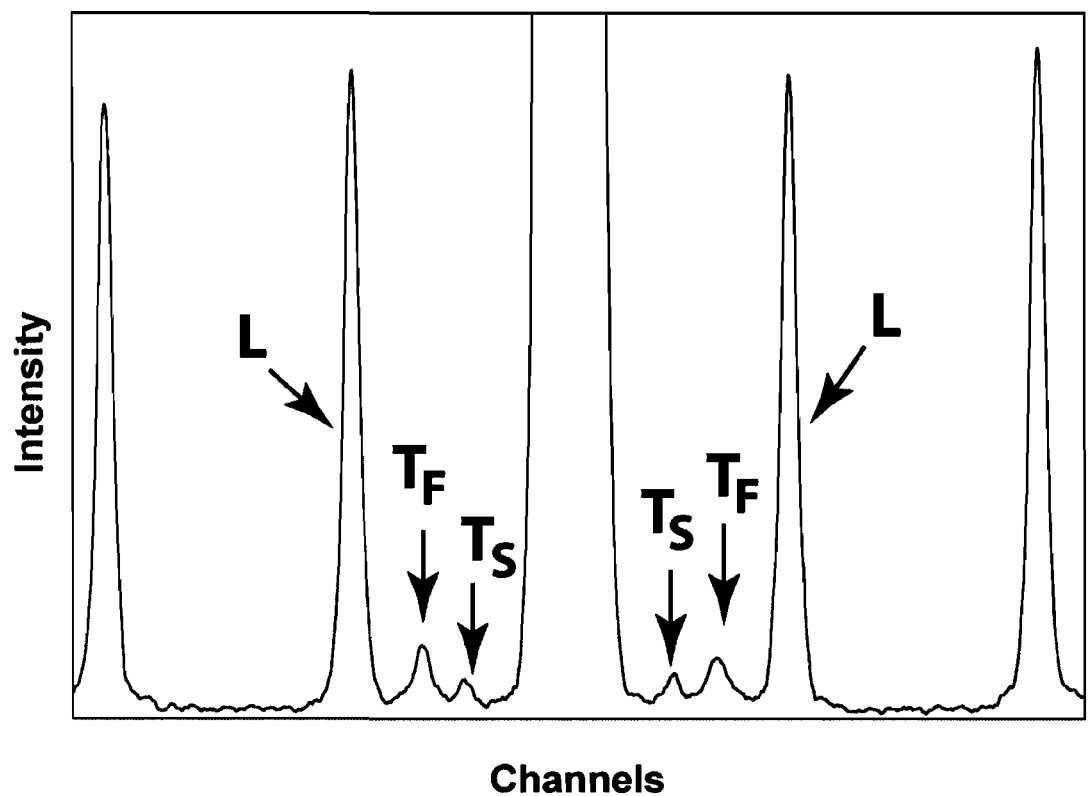
FIG. 3 is an example of a Brillouin spectrum of $\epsilon$-CL-20 for the (−0.9565, 0.0000, −0.2917) phonon, according to embodiments of the invention.

Results: An example Brillouin spectrum of ϵ-CL-20 is shown in FIG. 3. The quasi-transverse slow, quasi-transverse fast, and quasi-longitudinal modes are all clearly present. The minimized stiffness constants for Haycraft's work are presented in the first column of Table 1 in standard Voigt notation. For Haycraft's reported values, an over-determined set of 15 acoustic velocities measured in 7 symmetrically unique phonon directions was used in the least-squares minimization routine to solve for the stiffness constants. A density of 2044 kg/m$^3$ for ϵ-CL-20, calculated from the unit cell parameters obtained by x-ray diffraction, was used in the elastic constant calculation. Including an error of ±0.5° for angular crystal and polarization alignment and an error of ±0.003 cm$^{-1}$ for determination of the acoustic mode energy shifts, the uncertainties in the reported elastic constants are of the order of 0.06 GPa. The principal minors of the stiffness tensor determinant were found to be positive, ensuring the elastic constants represent a physically real system. The largest percent difference error between the calculated velocities and the experimental velocities was found to be 4.49% for the transverse slow mode of the (0.0000, 1.0000, 0.0000) phonon. The arithmetic average percent difference error between the calculated velocities and the experimental velocities was 1.75% for the transverse slow, 1.14% for the transverse fast, and 0.003% for the longitudinal modes. These small differences in error indicate excellent agreement between the measured and calculated acoustic velocities.

TABLE 1

Comparisons between the experimental and theoretical studies of the stiffness constants for ϵ-CL-20 at ambient conditions. The theoretical values have been transformed from a P2$_1$/a setting to the more common P2$_1$/n, for the purposes of direct comparison. In addition, Xu et al. only reported stiffness constants to one place past the decimal. The stiffness constants are given by $C_{ij}$.

| Elastic constants (GPa) | This work | Xu et al.[a] |
|---|---|---|
| $C_{11}$ | 7.70 | 15.1 |
| $C_{12}$ | 5.69 | 5.0 |
| $C_{13}$ | 9.21 | 8.0 |
| $C_{15}$ | 1.23 | −1.3 |
| $C_{22}$ | 28.29 | 18.1 |
| $C_{23}$ | −1.22 | 3.1 |
| $C_{25}$ | 1.01 | −3.2 |
| $C_{33}$ | 28.05 | 27.0 |
| $C_{35}$ | 3.07 | 4.6 |
| $C_{44}$ | 12.64 | 8.1 |
| $C_{46}$ | 0.74 | −1.1 |
| $C_{55}$ | 3.86 | 7.6 |
| $C_{66}$ | 4.73 | 3.8 |

[a]Reference 5.

Table 1 presents the stiffness constant data from Haycraft's work and the theoretical study published by Xu et al. They calculated the mechanical properties of a pure ε-CL-20 crystal and ε-CL-20 based plastic bonded explosives using molecular dynamics periodic computation, employing an advanced COMPASS force field. They estimated the mechanical properties by a static mechanic method utilizing the MATERIAL STUDIO 3.0.1 program. This particular force field has been utilized by Xu et al. on cyclotetramethylene tetranitramine (HMX), resulting in reported good agreement with experimental data. There are two general approximations for expressing the bulk modulus and the shear modulus. In the Voigt approximation, the polycrystal is composed of infinitely long single crystal fibers with different orientations. In the Reuss approximation, the polycrystal is composed of infinitely thin single crystal disks packed with different orientation, one upon the other. Using the Voigt approximation, where all crystallites undergo uniform strain, the expression for the bulk modulus ($B_V$) is $$B_v = \frac{1}{9}\sum_{i,j}^{3} C_{ij}, \quad (7)$$

and the shear modulus ($G_V$) is $$G_v = \quad (8)$$

$$\frac{1}{15}(C_{11} + C_{22} + C_{33}) - \frac{1}{15}(C_{12} + C_{23} + C_{13}) + \frac{1}{5}(C_{44} + C_{55} + C_{66}),$$

where $C_{ij}$ are the elastic constants from the stiffness tensor, in matrix notation. Using the Reuss approximation, where all crystallites undergo uniform stress, the expression for the bulk modulus ($B_R$) is $$B_R = \left(\sum_{i,j}^{3} S_{ij}\right)^{-1}, \quad (9)$$

and the shear modulus ($G_R$) is $$G_R = \left[\frac{4}{15}(S_{11} + S_{22} + S_{33}) - \right. \quad (10)$$

$$\left. \frac{4}{15}(S_{12} + S_{23} + S_{13}) + \frac{1}{5}(S_{44} + S_{55} + S_{66})\right]^{-1},$$

where $S_{ij}$ are the compliance constants from the compliance tensor, in matrix notation. Table 2 presents the bulk modulus and shear modulus using the Voigt and Reuss approximations, and arithmetic average (Voigt-Reuss-Hill) between the two approximations for the two sets of stiffness constants presented in Table 1.

TABLE 2

Comparisons between the ambient experimental and theoretical studies of the bulk (B) and shear (G) moduli for ε-CL-20.

| Moduli (GPa) | This work | Xu et al.[a] |
|---|---|---|
| $B_{Voigt}$ | 10.16 | 10.27 |
| $B_{Reuss}$ | 7.15 | 9.63 |
| Avg. | 8.65 | 9.95 |
| $G_{Voigt}$ | 7.60 | 6.84 |
| $G_{Reuss}$ | 3.76 | 5.41 |
| Avg. | 5.68 | 6.12 |

[a]Reference 5.

The Voigt bulk moduli calculated from Haycraft's experimental measurements show excellent agreement with the theoretical results reported by Xu et al., with a percent difference of 1.07%. The Voigt-Reuss-Hill shear and bulk moduli show fair agreement, as do the Voigt shear moduli. The remaining values show poor agreement with the highest deviation from Haycraft's work values occurring with the Reuss approximation of the shear modulus, with a difference of 30.5% with respect to the value calculated from the data reported by Xu et al. The agreement among the elements of the stiffness tensor varies widely between the two studies, as reported in Table 1. This work reports $C_{22}>C_{33}>C_{11}$, while Xu et al. report $C_{33}>C_{22}>C_{11}$. These values show poor agreement with the exception of $C_{22}$, which has a percent difference of only 3.74%. For the other three diagonal elements of the stiffness tensor, Haycraft's work reports $C_{44}>C_{66}>C_{55}$, while Xu et al. report $C_{44}>C_{55}>C_{66}$. Again, these values show poor numeric agreement, with the largest percent difference occurring for C55, with a value of 49.2%. The numerical agreement is fair for $C_{12}$, $C_{13}$, and $C_{66}$. Both studies find $C_{12}>C_{13}$, although the absolute magnitudes of $C_{13}$ and $C_{23}$ do somewhat vary. The values reported here for the stiffness constants differ from the previous theoretical study by Xu et al., with most of the values from Haycraft's work reported as higher than those reported earlier.

Discrepancies between the theoretical studies and Haycraft's experimental work are not unexpected. In general, theoretical studies make use of potentials that often very accurately reproduce the unit cell structure of a molecular system. However, this does not guarantee the curvature of the potential surface would accurately predict the vibrational frequencies or elastic properties of a given material, even if a particular potential was found to work well for a related material. Xu et al. reported good agreement with other researchers when applying their methods to HMX. However, HMX and CL-20 differ significantly in their molecular structures. Therefore, it is difficult to assert that prior success with HMX would guarantee accurate results with CL-20. As a consequence, theoretical reports on the types of properties discussed in this manuscript may not match well with experimental data.

Cauchy relations may be used to assess the anisotropy of the lattice potential. For a monoclinic space group, these relations are $C_{25}=C_{46}$, $C_{23}=C_{44}$, $C_{13}=C_{55}$, and $C_{12}=C_{66}$. For structures that are centrosymmetric and strictly follow a central potential, the elastic constants should be totally symmetric in their four suffixes. The further symmetry provided by the Cauchy relations reduces the maximum number of independent elastic constants from 21 to 15 for the totally general case. In crystal structures for which the Cauchy relations might be valid, the extent to which they are fulfilled is often used to assess the validity of assuming a central-force field.

For the ε-CL-20 stiffness constants reported in Haycraft's work, $C_{25}$ and $C_{46}$ differ by 26.7% and $C_{12}$ and $C_{66}$ by 16.9%. With $C_{13}$ and $C_{55}$ differing by 58.1%, and $C_{12}$ and $C_{66}$ not only differing by a substantial amount but also in sign, the use of Cauchy relations to describe ε-CL-20 will yield poor results. An analysis of the elastic constant data published by Xu et al. yields a similar conclusion. This is an indication that many-body forces will more accurately predict the properties of solid ε-CL-20.

Figure 4:
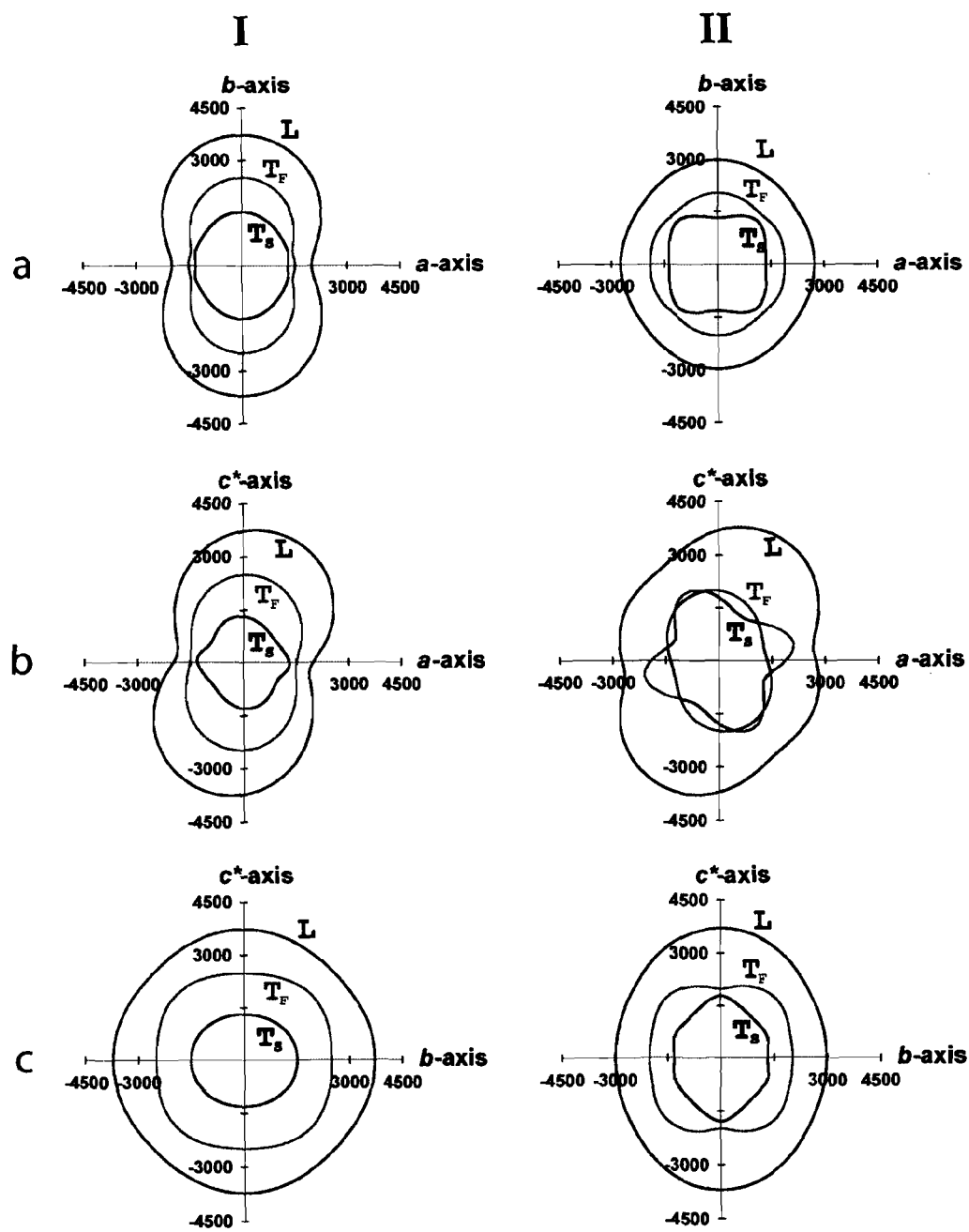
FIG. 4 includes sound velocity diagrams for $\epsilon$-CL-20 in the (a) ab-crystallographic plane, (b) ac*-crystallographic plane, and (c) bc*-crystallographic plane for Haycraft's work (I) and the theoretical work of Xu et al. (II), according to embodiments of the invention.

FIG. 4 gives the sound velocity diagrams of ε-CL-20 for the crystallographic ab-plane, ac*-plane, and bc*-plane for Haycraft's work (I) and the theoretical work of Xu et al. The transverse slow ($T_S$), transverse fast ($T_F$), and longitudinal modes (L) are labeled in each diagram is a two-dimensional slice that represents the velocity at which a sound wave propagates through the lattice in a given plane. Units are in m/s.

The sound velocity diagrams between Haycraft's work and Xu et al. show a number of differences in velocity. This is due to the numerical differences in the stiffness tensors. The ab-plane shows surface shapes and velocities differ substantially between the two studies. The bc*-plane shows similar velocities, but different surface shapes. The ac*-plane shows similar longitudinal shapes, but differing velocities. The differences in shape and velocity in the diagrams are directly tied to the reported stiffness tensors and the material's measured density.

Linear compressibility is a measure of how the lattice responds to a hydrostatic stress. The larger the value, the more compliant the lattice is along a given stress direction. The compressibility is a function of direction and can provide insight into the anisotropy of the strength of intermolecular interactions. A direction in which the intermolecular interactions are stronger would reflect a lower compressibility in that direction. The linear compressibility is calculated from $$\beta = \sum_i \sum_j s_{ijkl} q_i q_j, \quad (11)$$

where $S_{ijkl}$ represents the compliance tensor. A polar plot of Eq. (11) provides association of the entire compliance tensor and compressibility which portrays the tensor property rather than using single elements of the tensor that have a greater projection along a given direction.

Figure 5:
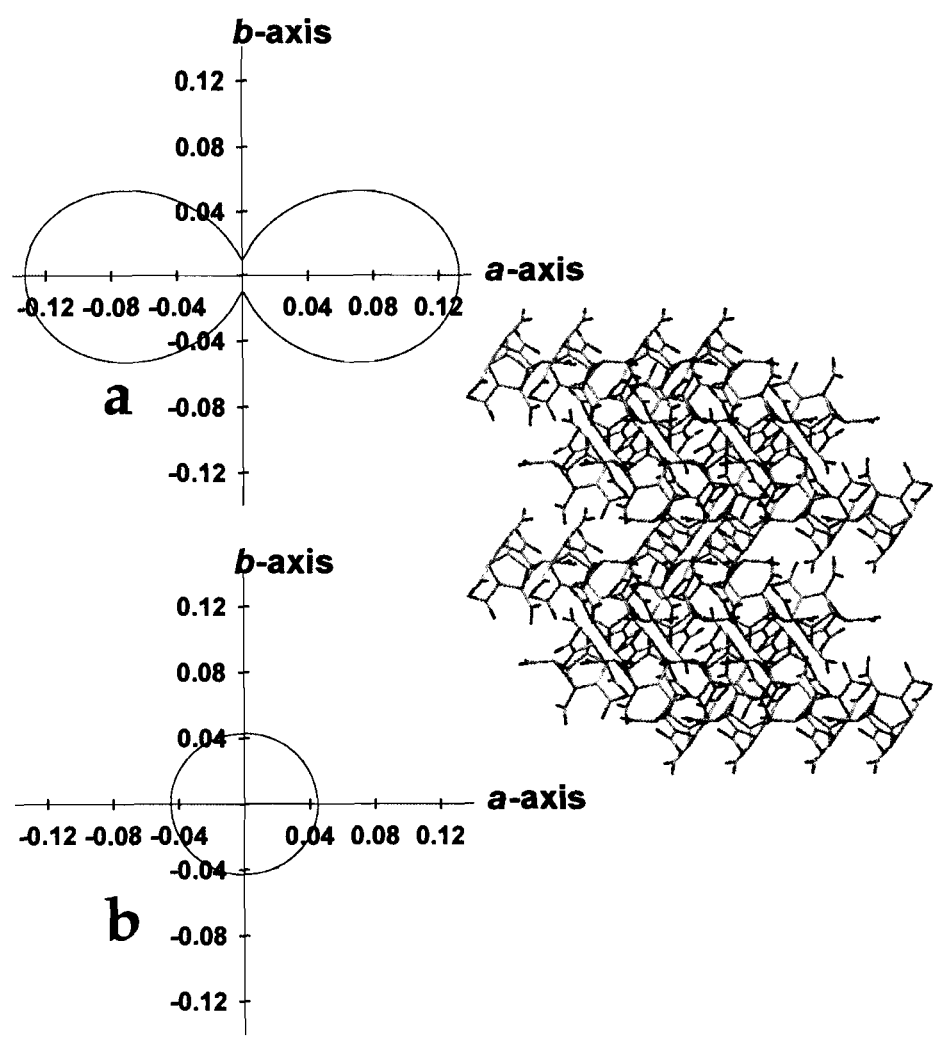
FIG. 5 includes linear compressibility diagrams for $\epsilon$-CL-20 in the ab-crystallographic plane for (a) Haycraft's work and (b) Xu et al, according to embodiments of the invention.
Figure 6:
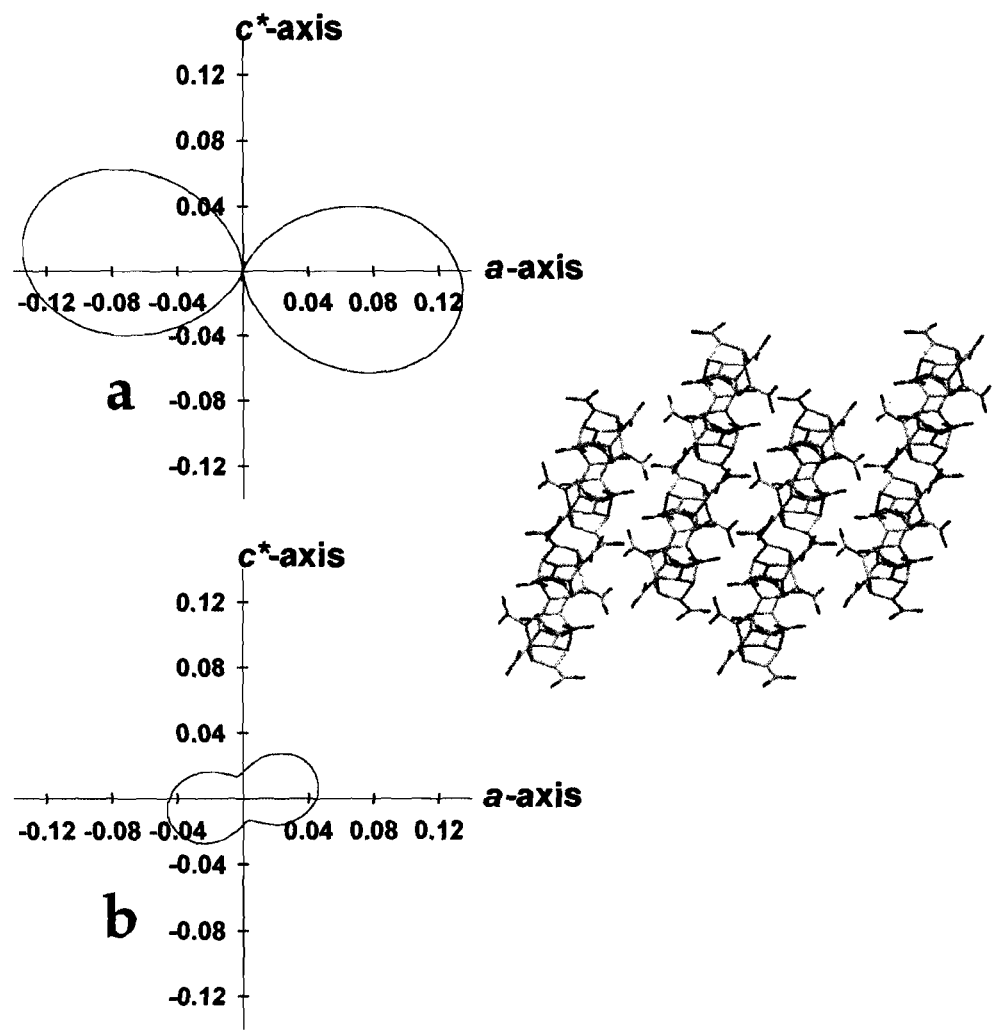
FIG. 6 includes linear compressibility diagrams for $\epsilon$-CL-20 in the ac*-crystallographic plane for (a) Haycraft's work and (b) Xu et al, according to embodiments of the invention.
Figure 7:
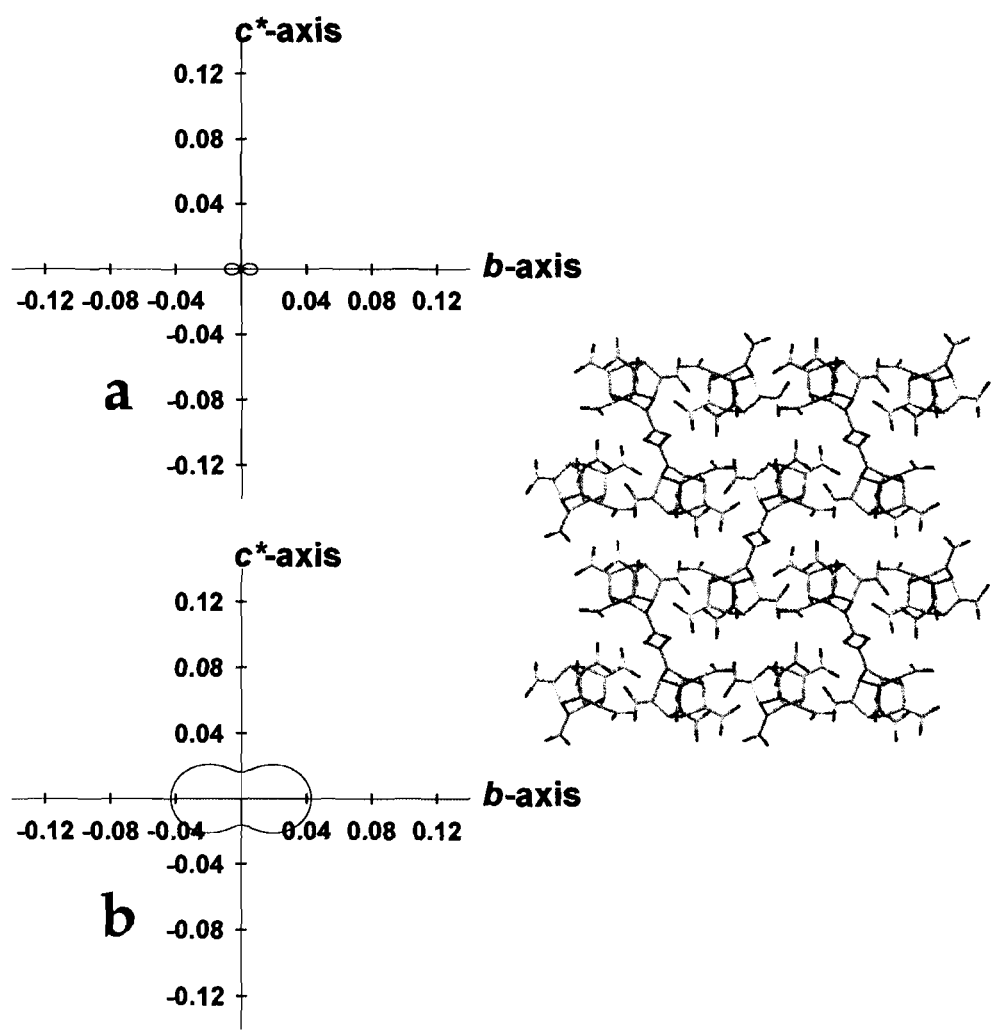
FIG. 7 includes linear compressibility diagrams for $\epsilon$-CL-20 in the bc*-crystallographic plane for (a) Haycraft's work and (b) Xu et al, according to embodiments of the invention.

FIG. 5 contains linear compressibility diagrams for ε-CL-20 in the ab-crystallographic plane for (a) Haycraft's work and (b) Xu et al. The projection of ε-CL-20 molecules in the unit cell for this plane is shown on the right hand side. Units are $GPa^{-1}$. FIG. 6 contains linear compressibility diagrams for ε-CL-20 in the ac*-crystallographic plane for (a) Haycraft's work and (b) Xu et al. The projection of ε-CL-20 molecules in the unit cell for this plane is shown on the right hand side. Units are $GPa^{-1}$. FIG. 7 contains linear compressibility diagrams for ε-CL-20 in the bc*-crystallographic plane for (a) Haycraft's work and (b) Xu et al. The projection of ε-CL-20 molecules in the unit cell for this plane is shown on the right hand side. Units are $GPa^{-1}$.

FIGS. 5-7 show the linear compressibilities of ε-CL-20 in each of the three crystallographic planes using the compliance tensors calculated from all of the elastic constant data listed in Table 1. The projection of ε-CL-20 in the unit cell in each of the three crystallographic planes is also included on the right side for each figure as a spatial reference.

The compressibility diagrams provide information on how easily the lattice deforms under a given hydrostatic stress. A circular plot indicates isotropic behavior under compression while plots that are elliptical indicate anisotropy in the compressibility. For the ab-crystallographic plane, the circular shape of Xu et al. indicates nearly isotropic behavior. The elliptical shapes displayed by Haycraft's work indicate a higher degree of compressibility along the a-axis. For the ac*-crystallographic plane, shown in FIG. 5, the elliptical shapes of Haycraft's work and Xu et al. indicate a deviation from isotropic compressibility in this plane. The more distorted oval shapes seen in Haycraft's work indicate a larger deviation from isotropic compressibility. Finally, for the bc*plane shown in FIG. 6, the presence of a very small ellipse for Haycraft's work shows that ε-CL-20 is highly incompressible in this plane. It can be seen from these plots that the data from this work, in general, predict highly anisotropic compressibility in the three crystallographic planes presented.

The nearly anisotropic compressibility calculated from the measured stiffness constants reported by Haycraft is in disagreement with recent theoretical and experimental work. Xu et al. published a report using density functional theory to investigate the structural and electronic properties of the four polymorphs of CL-20. In their study, they calculated the variations of the lattice parameters, unit cell volume, and density as a function of hydrostatic pressure for ε-CL-20. Their results show that for crystallographic a-axis and c-axis, nearly identical compressing of the lattice would be observed at very high pressure. When correlating the compressibility of a lattice constant with the strength of the intermolecular forces observed along that axis, it would be expected to see much lower compressibility for axes that contain a high number of intermolecular interactions. This can also be correlated with three of the diagonal elastic constants: $C_{11}$, $C_{22}$, and $C_{33}$.

In the study by Xu et al., for crystallographic a-axis and c-axis, since they have similar compressibilities, it would be expected them to have similar $C_{11}$ and $C_{33}$ elastic constants. This is simply not the case for extreme pressure; the $C_{11}$ and $C_{33}$ elastic constants of Xu et al. differ by 44%. For their data reported under smaller hydrostatic pressure conditions, the correlation is better. From 0 to 5 GPa, crystallographic a-axis compresses by 3.09%, crystallographic b-axis compresses by 2.53%, and crystallographic c-axis compresses by 2.07%. From this ordering it would be expected to see $C_{33}>C_{22}>C_{11}$ for the data presented by Xu et al., and in fact that is the case. Xu et al. also report percent difference relative to experimental data; however, these data were not given, so it is difficult to gauge the accuracy of their results for the higher pressure regimes.

In addition, it is highly unlikely that an organic crystal such as ε-CL-20 would survive to pressures of 400 GPa, as reported. Sorescu et al. also looked at theoretical compression studies of ε-CL-20. They used molecular dynamics and isothermal-isobaric molecular dynamics to calculate the changes in lattice parameters under hydrostatic compression. From 0 to 3.50 GPa, Sorescu et al report that crystallographic a-axis compresses by 2.98%, crystallographic b-axis compresses by 3.98%, and crystallographic c-axis compresses by 2.94%. These results would suggest an elastic constant ordering of $C_{33}>C_{11}>C_{22}$, the opposite from what is reported here. In addition, Sorescu et al. reported reasonable agreement with experimental data by Pinkerton. Pinkerton's preliminary data suggest an elastic constant ordering of $C_{11}>C_{33}>C_{22}$, with higher lattice compression than what was predicted by Sorescu et al. Gump and Peiris studied the phase stability of ε-CL-20 at high pressure and temperature. They performed compression experiments at ambient temperature and high temperature and concluded in both instances that the b-axis showed greater compressibility than either the a-axis or c-axis. This is a similar trend to what was predicted by Sorescu et al. Bolotina et al. studied the variable temperature crystal structures of two polymorphs of CL-20 from 100 to 298 K. ε-CL-20 was found to compress nearly uniformly in this temperature region. While this may suggest isotropic compressibility behavior, it is more likely that larger changes in temperature are needed to see the results provided by small amounts of hydrostatic pressure.

Comparison of ε-CL-20 to RDX and β-HMX

Table 3 lists the stiffness constants common between ε-CL-20, RDX, and β-HMX. Since RDX is an orthorhombic system, its stiffness tensor is comprised of only nine independent elastic constants. Thus, a direct comparison of all stiffness constants between the three materials is not possible. However, some observations may be made concerning some of the more prominent stiffness constants. The ordering of $C_{11} > C_{22} > C_{33}$ is common for both RDX and β-HMX, but not ε-CL-20. This illustrates that they have the strongest interactions along the a-crystallographic axis, while ε-CL-20 strongest interaction is along the b-crystallographic axis. β-HMX and ε-CL-20 both contain $C_{22}$ values that are internally similar to the $C_{33}$ values, suggesting a common degree of isotropy in those planes. While both RDX and β-HMX contain cleavage planes that correspond to some of their lowest stiffness constants, no such plane has been reported in ε-CL-20. The $C_{12}$ and $C_{13}$ values are also similar for β-HMX and ε-CL-20, but much lower for RDX. This suggests that β-HMX and ε-CL-20 will be less susceptible to specific shear deformations along the b- and c-crystallographic axes than RDX.

TABLE 3

Comparisons between common stiffness constants from Brillouin scattering studies on ε-CL-20, RDX, and β-HMX. β-HMX crystallizes in the monoclinic space group P2$_1$/n and RDX crystallizes in the orthorhombic space group Pbca.

| Elastic constants (GPa) | ε-CL-20 (this work) | RDX[a] | β-HMX[b] |
|---|---|---|---|
| $C_{11}$ | 7.70 | 36.67 | 18.41 |
| $C_{12}$ | 5.69 | 1.38 | 6.37 |
| $C_{13}$ | 9.21 | 1.67 | 10.50 |
| $C_{15}$ | 1.23 | ... | −1.1 |
| $C_{22}$ | 28.29 | 25.67 | 14.41 |
| $C_{23}$ | −1.22 | 9.17 | 6.42 |
| $C_{25}$ | 1.01 | ... | 0.83 |
| $C_{33}$ | 28.05 | 21.64 | 12.44 |
| $C_{35}$ | 3.07 | ... | 1.08 |
| $C_{44}$ | 12.64 | 11.99 | 4.77 |
| $C_{46}$ | 0.74 | ... | 2.75 |
| $C_{55}$ | 3.86 | 2.72 | 4.77 |
| $C_{66}$ | 4.73 | 7.68 | 4.46 |

[a]Reference 4.
[b]Reference 3.

Table 4 lists the bulk and shear moduli comparisons between ε-CL-20, RDX, and β-HMX. The Voigt bulk moduli between ε-CL-20 and β-HMX show excellent agreement, as do the Voigt-Reuss-Hill bulk moduli, which differ by 12.6%. Generally poor agreement is seen between RDX and ε-CL-20 for most of the moduli values. The Voigt-Reuss-Hill shear moduli for ε-CL-20 and β-HMX differ by 34.8%, both of which are smaller than the value for RDX. The larger shear modulus value for RDX indicates the solid is overall less susceptible to shear forces than ε-CL-20 and β-HMX.

Relevance to Shock Detonation Sensitivity

TABLE 4

Comparisons between the bulk (B) and shear (G) moduli obtained from Brillouin scattering studies on ε-CL-20, RDX, and β-HMX.

| Moduli (GPa) | ε-CL-20 (this work) | RDX[a] | β-HAM[b] |
|---|---|---|---|
| $B_{Voigt}$ | 10.16 | 12.05 | 10.20 |
| $B_{Reuss}$ | 7.15 | 11.92 | 9.60 |
| Avg. | 8.65 | 11.99 | 9.90 |
| $G_{Voigt}$ | 7.60 | 9.26 | 4.30 |
| $G_{Reuss}$ | 3.76 | 6.40 | 3.10 |
| Avg. | 5.68 | 7.83 | 3.70 |

[a]Reference 4.
[b]Reference 3.

It has been previously noted that the stiffer the lattice of a given energetic material, the less sensitive the material appears to be to detonation initiation from a hydrodynamic shock. From the three sets of elastic constants listed in Table 3, RDX can be considered to have the overall stiffest lattice. A recent report found HMX to be more sensitive to shock-initiated detonation than RDX, although no mention of lattice directional sensitivity was made. The elastic constants of ε-CL-20 are generally smaller than β-HMX, with a few exceptions. This would suggest that ε-CL-20 is more sensitive than β-HMX, and this has been shown to be true. Furthermore, the elastic constants of PETN are generally smaller than those of RDX, and slightly smaller than those of β-HMX and ε-CL-20. Of these four energetic materials, PETN is found to be the most sensitive to shock initiation. The association of lattice stiffness and orientation-dependent detonation sensitivity is observed for PETN, whose stiffest elastic constant is $C_{11}$ with the lowest detonation sensitivity along the (100) crystallographic direction. When this trend continues for secondary nitramine explosives, then ε-CL-20 should be most sensitive to detonation along the crystallographic a-axis and least sensitive along the b-axis.

The stiffness constants for ε-CL-20 have been successfully determined using Brillouin scattering. These constants were found to differ from those seen by other researchers, with values lying generally greater than those reported in the other work. These measurements indicate that ε-CL-20 is stiffest along the crystallographic b-axis, followed by c-axis and then a-axis. The linear compressibility diagrams indicate anisotropic compressibility under moderate applied pressures, which differs from theoretical and experimental reports from other researchers. Additional studies will need to be conducted to rectify the differences between the experimental and theoretical studies on the compressibility of ε-CL-20.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

This invention is used to measure the major and minor axes of the optical indicatrix of a single crystal of material at a very specific wavelength. This process is repeated for each crystal face in order to form a complete picture of the refractive index for the sample. This is most useful for anisotropic materials of low symmetry, where the maximum value of the refractive index does not align with crystal axis. The refractive indices measured in this experiment are used directly in Brillouin Scattering Spectroscopy, Raman Spectroscopy, resonance Raman spectroscopy, coherent anti-Stokes Raman spectroscopy, surface-enhanced Raman spectroscopy, and piezo-Raman spectroscopy.

There are a number of commercial products available to measure the bulk refractive indices of liquids. A small number of products are available to measure the bulk refractive index of a solid sample. Currently there are no instruments available that measure the optical indicatrix of a crystalline sample, using reflected light from the surface of the sample.

Companies that would be interested in this technology would include precision instrument manufacturers. This list would include: Perkin-Elmer, Princeton Instrument, Texas Instruments, McPherson, Nicolet, Enwave Optronics, and Horiba Jobin Yvon.

Major advantages of the invention include, but are not limited to the ability to probe the reflectivity of a surface at specific wavelengths, precise control of the sample's orientation with respect the electric vector of the incoming light, and the flexibility provided by the design with respect to possible light sources and detectors.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. An apparatus, comprising:
   a device that holds and/or suspends a sample in position to be analyzed, and a rotating device, wherein said sample can be moved and rotated into a stationary position;
   an adjustable source that produces light;
   an optical chopper, wherein said light is directed through said chopper, wherein said light exiting from said chopper provides a signal reference for experimentation;
   at least one mirror that directs light and aligns said light with said sample;
   a first iris and a second iris;
   a first polarizer and/or polarization device; and a second polarizer and/or polarization device;
   a first lens, a second lens and a third lens, wherein said light is directed through said first iris, said first polarizer and/or polarization device, and said first lens;
   a beam sampling device, wherein said device reflects a small portion of said light towards said sample, wherein said light reflects off said sample and through said second lens, said second polarizer and/or polarization device, said second iris and said third lens;
   a visualization device, wherein said light is directed through said visualization device;
   a data collection system; and
   a light sensing detector and a photomultiplier power supply, wherein after data is collected, light impacts said light sensing detector and said photomultiplier power supply energizes said light sensing detector creating a current signal.

2. The apparatus according to claim 1, wherein said device that holds and/or suspends said sample includes a multi-axis translator system.

3. The apparatus according to claim 1, wherein said data collection system is performed by personal computer and/or direct visualization.

4. The apparatus according to claim 1, wherein said sample is a crystalline.

5. The apparatus according to claim 4, wherein said apparatus measures the surface reflectivity of said crystalline sample.

6. The apparatus according to claim 1, wherein said source is a pulsed light source, and wherein said optical chopper is replaced by a polarization scrambler.

7. The apparatus according to claim 1, further comprising a first diffuser and a second diffuser.

8. The apparatus according to claim 7, further comprising a first light tube and a second light tube, wherein said light is directed through said first light tube a first lens, a second lens and a third lens, wherein said light is directed through said first iris, said first polarizer and/or polarization device, said first diffuser, said first lens, said second diffuser, and said second light tube.

9. The apparatus according to claim 1, wherein said visualization device is a microscope assembly.

10. The apparatus according to claim 1, wherein said light sensing detector and said photomultiplier power supply, wherein after data is collected, light impacts said light sensing detector and said photomultiplier power supply energizes said light sensing detector creating a current signal; and a pre-amplifier, wherein said current signal is channeled to said pre-amplifier which said current signal is converted to a voltage signal which is amplified.

11. The apparatus according to claim 1, further comprising a digital locking amplifier.

12. The apparatus according to claim 1, further comprising a digital oscilloscope.

13. A method for measuring surface reflectivity of a crystalline sample, comprising:
   producing light;
   directing said light through an optical chopper, modulating said light by said chopper, wherein said modulated light from said chopper provides a referencing signal;
   aligning said modulated light by mirror(s) with the sample and collection optics;
   directing said light through a first iris, a first polarizer and/or polarization device, a first lens;
   reflecting a small portion of said light toward said crystalline sample by a glass pick-off;
   mounting said crystalline sample on a device that holds and/or suspends said crystalline sample in a position to be analyzed, and a rotating device, wherein said crystalline sample can be moved and rotated into a stationary position;
   rotating said device that holds and/or suspends said crystalline sample to place said crystalline sample in a desired stationary position for analyzing;
   directing said light to reflect off of said crystalline sample;
   directing said light through a first lens, a second polarizer and/or polarization device, a second iris, and a second lens;
   directing said light through a microscope assembly
   observing said light through said microscope assembly;
   collecting data from findings of observing said light through said microscope assembly;
   impacting said light onto a photomultiplier tube or other suitable detector;

energizing said light/photomultiplier tube by said photomultiplier power supply which alters said light to a current signal;

channeling said current signal to a pre-amplifier and converting said current signal into a voltage signal and amplifying said voltage signal;

channeling said amplified voltage signal to an optional digital locking amplifier and recording said amplified voltage signal; and channeling said amplified voltage signal to a digital oscilloscope and monitoring the modulated signal.

14. The method according to claim 13, wherein said device that holds and/or suspends a sample includes a multi-axis translator system.

15. The method according to claim 13, wherein said data collection system is performed by a computer or direct visual observation.

16. The method according to claim 13, further comprising directing said path of light through a light tube.

17. The method according to claim 13, wherein said optical chopper is replaced by a pulsed light source and a polarization scrambler.

* * * * *